United States Patent
Kraus et al.

(10) Patent No.: US 6,804,559 B1
(45) Date of Patent: Oct. 12, 2004

(54) ELECTROMEDICAL IMPLANT

(75) Inventors: Michael Kraus, Forchheim (DE);
Martin Lang, Grossenseebach (DE);
Berhard Lang, Feucht (DE); Johannes Neudecker, Erlangen (DE); Klemens Beetz, Erlangen (DE); Axel Nagelschmidt, Erlangen (DE); Jens Potschadtke, Erlangen (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/603,812

(22) Filed: Jun. 26, 2000

(30) Foreign Application Priority Data

Jun. 25, 1999 (DE) .......................................... 199 30 245

(51) Int. Cl.⁷ .............................................. A61N 1/362
(52) U.S. Cl. ........................................... 607/32; 607/60
(58) Field of Search ....................... 607/30–32, 59–60, 607/66, 33; 128/903

(56) References Cited

U.S. PATENT DOCUMENTS

| | | |
|---|---|---|
| 4,166,470 A | 9/1979 | Neumann |
| 4,172,459 A | 10/1979 | Hepp |
| 4,531,527 A | 7/1985 | Reinhold, Jr. et al. |
| 4,741,341 A | 5/1988 | Marach ..................... 128/419 |
| 5,127,404 A | 7/1992 | Wyborny et al. |
| 5,139,028 A | 8/1992 | Steinhaus et al. |
| 5,197,480 A | 3/1993 | Gebhardt |
| 5,246,008 A | 9/1993 | Mueller |
| 5,292,343 A | 3/1994 | Blanchette et al. |
| 5,313,953 A | 5/1994 | Yomtov et al. |
| 5,348,008 A | 9/1994 | Bornn et al. |
| 5,411,031 A | 5/1995 | Yomtov |
| 5,411,536 A | 5/1995 | Armstrong |
| 5,413,594 A | 5/1995 | Williams |
| 5,522,396 A | 6/1996 | Langer et al. |
| 5,531,774 A | * 7/1996 | Schulman et al. ............. 607/56 |
| 5,562,713 A | 10/1996 | Silvian |
| 5,626,630 A | 5/1997 | Markowitz et al. |
| 5,702,431 A | 12/1997 | Wang et al. |
| 5,720,770 A | 2/1998 | Nappholz et al. |
| 5,729,203 A | 3/1998 | Oka et al. |
| 5,735,887 A | * 4/1998 | Barreras et al. ............... 607/60 |
| 5,752,976 A | 5/1998 | Duffin et al. |
| 5,814,089 A | 9/1998 | Stokes et al. |
| 5,999,857 A | * 12/1999 | Weijand et al. ................ 607/60 |

FOREIGN PATENT DOCUMENTS

| | | |
|---|---|---|
| DE | 31 39 452 | 9/1982 |
| DE | 39 36 547 | 5/1991 |
| DE | 43 41 903 | 6/1995 |

(List continued on next page.)

OTHER PUBLICATIONS

The Vibrator Power Supply, pp. 1–6.*
Corresponding European Patent Office search report, dated Dec. 4, 2003, for Application No. 00250200.3.
Duisters et al., "A –90 dB THD Rail–to–Rail Input Opamp Using a New Local Charge Pump in CMOS", IEEE J. of Solid–State Circuits, vol. 33, No. 7, Jul. 1998, pp. 947–955.
"Read Only Contactless Identification Device", UEM: EM Microelectronic–Marin, SA, Paper No. H4102, Marin, Switzerland, 2000, pp. 1–6.

*Primary Examiner*—George R. Evanisko
(74) *Attorney, Agent, or Firm*—Christie, Parker & Hale, LLP

(57) ABSTRACT

An electromedical implant comprising a telemetry device for the exchange of data with an external apparatus is provided. The telemetry device comprising a transmitting device and a receiving device, wherein a separate energy storage means is provided for each of the transmitting device and the receiving device. A method of using an electromedical implant comprising a telemetry device for the exchange of data is also provided.

10 Claims, 10 Drawing Sheets

FOREIGN PATENT DOCUMENTS

| | | |
|---|---|---|
| DE | 689 22 362 | 8/1995 |
| DE | 196 22 154 | 5/1997 |
| EP | 0 097 264 | 1/1984 |
| EP | 0 340 293 | 11/1989 |
| EP | 0 344 770 | 12/1989 |
| EP | 0 362 611 | 4/1990 |
| EP | 0 450 341 | 10/1991 |
| EP | 0 537 936 | 4/1993 |
| EP | 0 540 154 | 5/1993 |
| EP | 0 607 638 | 7/1994 |
| EP | 0 856 333 | 8/1998 |
| WO | WO91/16696 | 10/1991 |
| WO | WO 97/00708 | 1/1997 |
| WO | WO 98/08567 | 3/1998 |
| WO | WO 98/42407 | 10/1998 |

* cited by examiner

ELECTROMEDICAL IMPLANT

FIELD OF THE INVENTION

The invention concerns an electromedical implant comprising a telemetry device for the exchange of data with an external apparatus and more particularly to a cardiac pacemaker comprising such a telemetry device.

BACKGROUND OF INVENTION

In conventional electromedical implants with a telemetry device for the exchange of data with an external apparatus, such as, for example, cardiac pacemakers, defibrillators, cardioverters or other electronically actuated or controlled implants, the energy for transmission and reception for the telemetry device, including a transmitting device and a receiving device, is usually taken from a previously charged buffer capacitor.

In such a system, if transmission and reception follow in direct succession, the buffer capacitor has to be charged up to a high voltage to have sufficient voltage ready for the second procedure after the voltage drop resulting from the first procedure. Accordingly, the components involved (charge pump, capacitors, voltage regulator) must be designed for a voltage strength which would otherwise not be required in the implant. Such high voltage components increase the implant production costs. In addition, energy is lost because of the poor efficiency of voltage multiplication, which is a problem given the severely limited energy supply in an implant of that kind.

Accordingly, the need exists for an telemetry capable electromedical implant having lower production costs and which has lower energy requirements.

SUMMARY OF THE INVENTION

The invention is directed to an electromedical implant comprising a telemetry device for the exchange of data with an external apparatus where the telemetry device comprises a transmitting device and a receiving device, characterized in that separate energy storage devices are provided for the transmitting and receiving devices.

In such an apparatus, lower production costs and lower energy requirements are obtained if separate energy storage means are provided for the transmitting device and the receiving device, because the separate energy storage means only have to be charged to the voltage necessary for the single procedure involved. Furthermore, less energy is lost through voltage multiplication. Finally, the energy consumption involved in transmission does not influence the energy supply for reception and vice versa so that the procedures can occur in immediate succession, which is desirable for a bidirectional communication protocol. In this respect, an electromedical implant according to the invention is a particularly advantageous in the area of long-range high-frequency telemetry.

In one alternative embodiment, the individual energy storage means are formed by a buffer capacitor. In such an embodiment, the buffer capacitors may be of different sizes and the size of the buffer capacitors are matched to the procedure which is to be supplied thereby, e.g., if a transmission procedure should requires more power than a reception procedure.

In another alternative embodiment, the buffer storage means may be designed such that they can both be charged at the same time depending on the requirements involved in unidirectional or bidirectional operation of the telemetry. In this respect, the buffer storage means are preferably charged immediately prior to a transmission procedure or a reception procedure in order to avoid the energy losses due to loss currents that can occur during relatively long periods of maintaining the charged state.

In still another alternative embodiment, one energy storage means is utilized as a safety reserve for the other energy storage means to improve transmission reliability. In such an embodiment, it is possible for the energy supply to be better utilized because, there would be no need to keep an additional safety reserve capacitor available for use after draining the first energy storage means.

In yet another alternative embodiment, it is possible to implement changes in the utilization of energy from a particular energy storage means using the circuit according to the invention. For example, in one exemplary embodiment, after draining the transmission energy storage means, the circuit could instruct the reception energy storage means to provide power for a renewed safety data transmission operation.

BRIEF DESCRIPTION OF THE DRAWINGS

Other advantageous developments of the invention are characterized in the appendant claims and are described in greater detail hereinafter together with the description of the preferred embodiment of the invention, with reference to the accompanying drawings in which:

DETAILED DESCRIPTION OF THE INVENTION

The present invention is directed to an electromedical implant comprising a telemetry device for the exchange of data with an external apparatus where the telemetry device comprises a transmitting device and a receiving device, characterized in that separate energy storage devices are provided for the transmitting and receiving devices.

Figure 1:
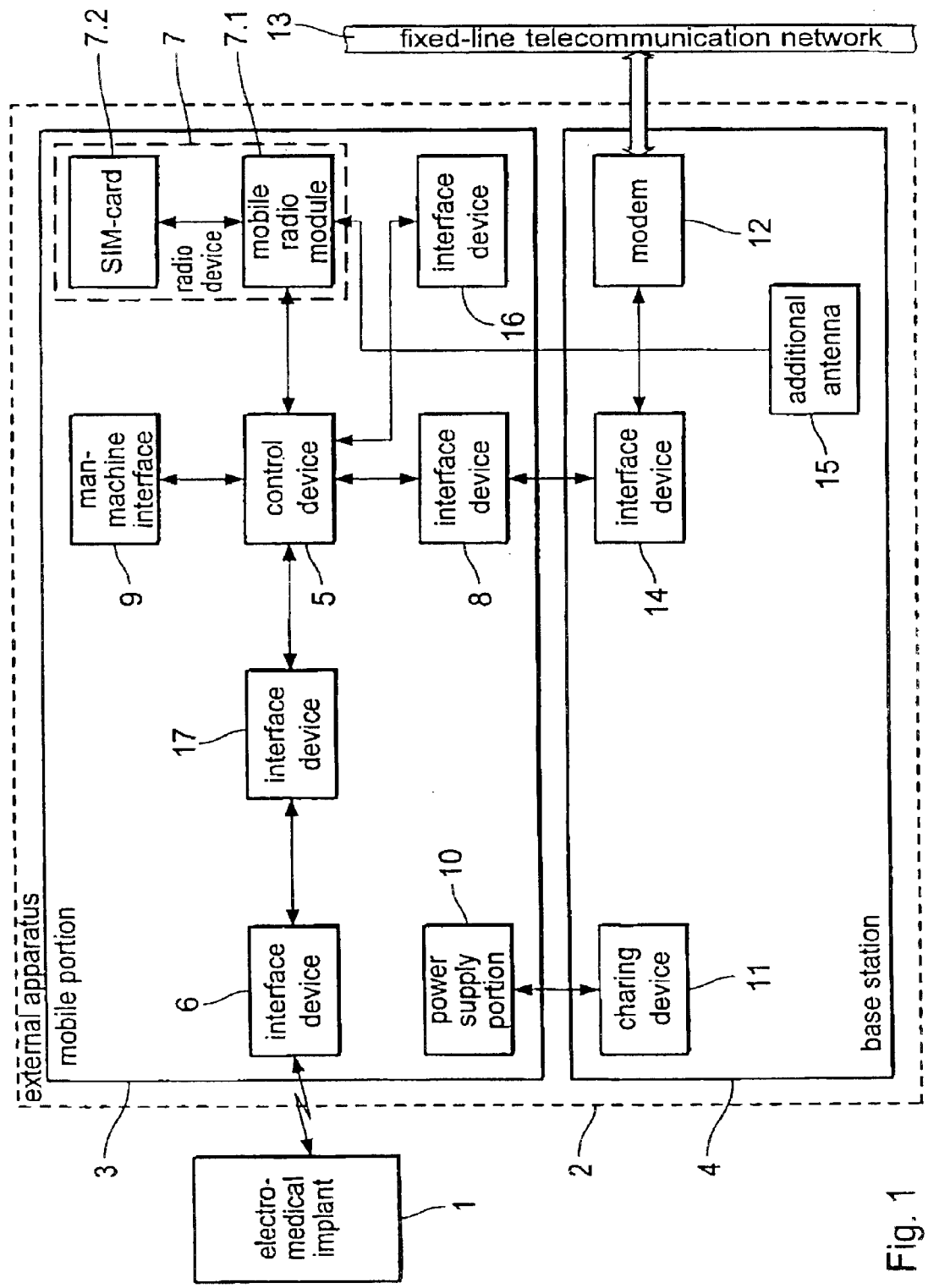
FIG. 1 shows a block circuit diagram of an embodiment of an apparatus according to the invention.

FIG. 1 shows a block-circuit diagram of an electromedical apparatus according to the invention comprising an electromedical implant 1, provided with a telemetry device (not shown) and an external apparatus 2 which itself comprises a mobile portion 3 and a base station 4.

In this arrangement, the mobile portion 3 has a control device 5 and a first interface device 6, a mobile radio device 7, a second interface device 8, a man-machine interface 9 and a third interface device 16 which are respectively connected to the control device 5. In this embodiment, the first interface device 6 is connected to the control device 5 indirectly by way of a further interface device 17. The power supply for the mobile portion is provided by Li-ion batteries which are disposed in the power supply portion 10.

The first interface device 6 comprises a telemetry transmitter-receiver unit so that the mobile portion 3 can make contact with the implant 1 by way of a bidirectional telemetry section interface device 6. The receiver and the transmitter of the interface device 6 are integrated in an IC. The two circuit portions form a functional unit. The receiver and the transmitter preferably operate in the UHF-range at 403.55 MHz, while the baud rate stages are 4, 8, 16 and 32 Kbit/s. It is, however, also possible to use energy-saving frequencies in the VHF- or LF-range, particularly for the implant.

The mobile radio device 7 can transmit data which are read out of the implant by way of the first interface device 6 in any suitable format, such as, for example, in the form of SMS-messages. In this embodiment, the mobile radio device 7 can be called by an outside service center serving as a monitoring or central storage service.

As shown in the embodiment of FIG. 1, a connection can also be made between the mobile portion 3 and the base station 4 by way of the second interface device 8 in the form of an infrared interface (IrDA). In this embodiment the second interface device 8 operates bidirectionally and can transmit data in the half-duplex mode.

In this embodiment, the man-machine interface 9 makes it possible for the mobile portion 3 to be operated by a user. In such an embodiment, the third interface device 16 is used for either receiving external data or for service. This interface is also in the form of an IrDA interface.

The Serial interface for both IrDA interface devices 8 and 16 and the interface to the mobile radio device 7 are disposed in parallel so that only one unit is operated at a time. The IrDA interfaces 8 and 16 are also connected in parallel. Both interfaces are continuously ready for reception so that an external request can be serviced at any time. During operation, the software then only has to establish at which IrDA interface the reception request occurred.

The power supply 10 for the mobile portion 3 is implemented by means of Li-ion batteries. In a fully charged state, such batteries can power the mobile portion 3 for at least 20 hours (standby time+16 SMS-transmissions). The size of the batteries determines the operating life of the device. As such, the arrangement preferably has a 1000 mAh Li-ion battery.

In a further embodiment, which is not specifically illustrated, the telemetry unit 6 for communication with the implant 1 including a transmitting/receiving antenna and an electronic actuating system for telemetry is disposed in a separate module. In such an embodiment, the separate module also has an interface device 17 for electrical and possibly also mechanical connection to a mobile telephone.

In such an embodiment, the separate module can be fitted into the mobile telephone in place of the phone's battery pack, thus affording a mechanically sturdy unit comprising the mobile telephone and a separate housing for the telemetry unit 6. In such an embodiment the separate housing for the telemetry unit 6 may extend to an immaterial degree beyond the previous external contour of the mobile telephone.

In this variant, the separate module for the telemetry unit 6 has a battery compartment into which can be fitted the original battery pack of the mobile telephone or alternatively another suitable battery or battery pack. In either case, the battery then serves as the power supply for the entire system including the mobile telephone and the separate module, and can be charged by way of the standard charging connections on the mobile telephone.

In this alternative embodiment, there are three basic options for providing data connection between the separate module and the mobile telephone: 1) by way of the external electromechanical plug of the interface provided on the mobile telephone (usually serial); 2) by way of an electromechanical plug of the (serial) interface provided on the mobile telephone, which plug is additionally integrated into the battery compartment of the mobile telephone; or 3) by way of an IrDA interface provided on the mobile telephone.

In the case of the first and third variants, there is an optical or mechanical connection between the separate module and the interface integrated in the mobile telephone, i.e., the separate module or a fixed extension thereof covers the interface of the mobile telephone and at that location either includes a suitable plug connection, or extends into the proximity of the interface of the mobile telephone and includes at that end an infrared interface. These solutions involve utilizing special software for the mobile telephone that permits control to be initiated by way of that interface.

For integration of the plug in the battery compartment, the second variant additionally requires a mechanical and electrical modification to the mobile telephone. A suitable connection of the plug not only to the serial interface, but also to other parts of the electronics of the mobile telephone, means that it is possible to provide direct control of the mobile telephone through the telemetry unit.

In both cases, the known normal function of the mobile telephone is retained although priority control for telemetry transmissions can possibly be provided. Preferably, the electronics of the mobile telephone are automatically set into operation when required by the telemetry unit, which is either permanently in a state of reception readiness, or which is selectively time-controlled (event control).

In another alternative embodiment, the separate module can be integrated on an SIM-card. In this embodiment, the SIM-module replaces the standard SIM-card in the SIM-card tray and uses the interface provided the standard SIM-card. For example, the transmitting/receiving antenna and the electronic actuating system for telemetry can be so designed that, when the SIM-module is inserted, they are disposed outside the housing of the mobile telephone.

In this embodiment, a buzzer, which is standard in mobile telephones, can be actuated for acoustic display of the various patient alarm functions. The optical display, which is also provided on mobile telephones can be used for the optical display, in all modular variants.

Such optical and acoustic alarms are to also supplied on standard designs of the current invention. For example, an LED and a buzzer for optical and acoustic display of functions and operating states, as well as some switches for manually triggering functions are provided on the mobile portion 3.

In one embodiment, a flashing light-emitting diode indicates a low battery state as soon as the battery charge has fallen to 10%. At this stage of discharge the mobile portion 3 still has a minimum running reserve of about 2 hours. As the mobile portion 3 is not always visible to the patient, the buzzer, by a short alarm, also indicates the occurrence of a low battery state. The buzzer must operate at a frequency of about 2 kHz or below and must be suitably loud so that even patients of limited perception can be certain to hear the alarm sound. The buzzer should trigger an alarm approximately every 5 minutes to remind the patient to charge up the battery.

A recessed on/off switch which cannot be unintentionally operated is also provided. The switch position is labeled so that it is possible to see whether the mobile portion 3 is switched on. That switch is necessary as the mobile portion 3 with the mobile radio device 7 must be switched off in some areas, such as, for example, in an in-flight situation and in certain areas of hospitals.

In addition, a key may be provided for sending short messages to the service center to test the SMS-channel. In such an embodiment the mobile portion 3 shows by means of a flashing LED that such a test has been started. The service center recognizes the received short message as being a test and sends an acknowledgment to the mobile portion 3. The LED is thereupon deactivated, whereby the patient can see that both the outgoing and also the incoming connection to the service center are operable.

For diagnostic purposes, there can also be provided a key by means of which the patient can trigger data transmissions to the service center. If the patient suffers from troubles of any kind which possibly cannot be in any way detected that key can be pressed. Thereupon a data set is transmitted, which, in addition to the items of information which are to be transmitted as a routine matter, includes the time of triggering and acquisition of the associated data by the implant. The transmitted short message also informs the service center that this is a patient-triggered data transmission which is to be dealt with separately.

For acute emergency cases, it is possible to use a patient alarm key which is also protected from unintentional incorrect operation. That emergency key can be arranged in recessed relationship for that purpose and can be additionally protected by a cover which first has to be opened in order to trigger the patient alarm. Alternatively, the protection against incorrect operation can also be in the form of a time lock in the software which assumes the key function to be valid only if the key is depressed for a relatively long period of time (for example more than 3 seconds). A successfully triggered patient alarm is acknowledged acoustically by the buzzer. Thereafter, the key can be released again. In addition, a light-emitting diode is continuously switched on for 10 seconds and then lights up once again for 2 seconds each minute as a reminder that a patient alarm has been triggered. The buzzer is always actuated simultaneously with the light-emitting diode so that even patients of limited optical perception can perceive this acknowledgment from the external apparatus.

A patient alarm is immediately transmitted to the service center by way of SMS. It is canceled only when the service center acknowledges the patient alarm—also by way of SMS—, thereby ensuring that the alarm has reached the service center. Acknowledgment of the alarm by the service center is also displayed by a light-emitting diode and a buzzer on the mobile portion 3. Those measures contribute on the one hand to calming the patient, while on the other hand ensuring that, upon triggering of a patient alarm in a dangerous condition for the patient, further measures are implemented if the patient alarm could not be transmitted successfully.

If a patient alarm, which has not been acknowledged is to be canceled, the mobile portion 3 has to be switched off. After the restart, the mobile portion is in the normal state again. The mobile portion automatically signals back to the service center by way of SMS. In the service center, it can then be recognized that the external apparatus was reset and the patient alarm canceled.

Successful implementation of a patient alarm has a higher priority to a low battery display. The low battery display is only implemented again when the service center has acknowledged the patient alarm. The mobile portion 3 is to be switched off if disturbance to the surrounding area by the buzzer is to be prevented.

Only one processor, which performs both the tasks of the central unit and also those of the communication unit, is used as the control unit 5 for the mobile portion 3. The software can be downloaded by way of the IrDA interface 16 into a flash-ROM. The memory capacity of the internal flash-ROM is 128 KBytes, that of the integrated EEPROM is 4 KBytes and that of the static external SRAM is 64 KBytes. The program memory size is thus limited to the capacity of the installed flash-ROM and cannot be expanded (Harvard structure). The external static SRAM can be expanded.

SMS-transmission is implemented using a 128 bit DES encryption process which is based on a private-public key system. Encryption is implemented in software terms, i.e., no encryption IC is used. For safe operation, the system uses a watchdog circuit which at regular intervals checks the processor 5 and puts it into a secure status again if program execution is not taking place correctly.

No further encryption is required between the implant 1 and the external apparatus 2 because of the short range and the implant-specific encoding of the data.

The field strength information with the associated numbers of the current and adjoined cells and the bit error rate is transmitted by way of SMS from the mobile radio device 7. Utilizing this position-finding information it is possible to locate the mobile portion 3 in emergency situations where the patient is incapacitated.

The mobile radio device 7 also includes a mobile radio module 7.1 and a memory in the form of a SIM(subscriber-Identity Module)-card 7.2. The SIM-card reader can-be soldered directly into the circuit board under the mobile radio module 7.1. The SIM-card 7.2 is thus not accessible to the user. Regardless, an SIM-card reader is provided in embodiments which are based on the use of a mobile telephone.

The call number or numbers of the service center are permanently stored in the memory of the SIM-card 7.2 by the mobile radio module 7.1. The mobile portion 3 is supplied with a SIM-card which contains the call number of a service center in the call number memory as a preset parameter. The call numbers on the SIM-card can be altered by way of SMS. Call number management (writing and reading the numbers on and from the SIM-card) must be implemented by the central control device 5 of the external apparatus. The preset call number is kept permanently on the SIM-card in another memory location and is used if the external apparatus 2 cannot form a connection with a new call number. This safety measure ensures that establishing contact always remains possible.

It is also possible to operate a plurality of service centers. In this case the patient reports to any service center. In that way the address of the customer is known there and it is possible to decide which service center initially takes over the procedure. If the customer switches on his external apparatus, then it reports to the preset service center insofar as it immediately sends an SMS-message thereto. Then, by sending back an SMS-message, the service center can transmit the call number which is to be used in future. The mobile portion 3 can thus be automatically associated at any time with another service center without a service engineer having to convert the mobile portion 3. Utilizing this system it is possible thereby to avoid having to send SMS-messages over frontiers.

The databases of the service centers are the same as each other so that it is always clear which implant 1 or mobile portion 3 is being operated by which service center. To ensure this, suitable fields are to be provided in the database.

During operation it is possible in each case to pick up only one further (second) number. This number is used if the contact with the "new" service center can be successfully achieved. If that is not the case, the "old" call number is used again. If the external apparatus is referred to a further service center, the second number is overwritten so that the operating procedure involved is always that first the second number is tried and, in the event of one or more abortive attempts, the first number is used. The advantage of this procedure is that it is possible to achieve full flexibility, but also to ensure that the secure call number remains stored so that a complete collapse of the connection is reliably avoided.

An LIFO-memory can also be organized in the SIM-card, for a maximum memory depth (for example ten call numbers). If the previously operative service center presets a new call number, that number is used as the most up-to-date call number. However, if transmission problems occur with that new call number, then in each case the next older call number is used until finally the permanently stored preset call number is used. If the memory is occupied, for example with 9 call numbers and the preset call number, then the oldest, that is to say the call number which is closest to the preset number is erased. The advantage of this procedure is its high level of redundancy as it is almost certain that a connection will occur with at least one of the stored service centers. The disadvantage is that under some circumstances many service centers receive data from an external apparatus, which only then can be combined together and evaluated jointly.

Because the external apparatus 2 is equipped with a modem 12 the call number memory in the SIM-card can also be used for those call numbers. The organization can be implemented based on the management of the mobile radio numbers. Because the call numbers are stored on the SIM-card, in the event the external apparatus is replaced by the customer, for example in the event of a defect, the SIM-card can be fitted into the new apparatus so that the connection to the service center is implemented without any gap or interruption.

The base station 4 comprises a charging device 11 for the batteries in the power supply portion 10 and a modem 12, acting as a data transmission device, for the fixed-line telecommunication network 13 which is addressed by the mobile portion 3 by way of the interface device 14. The base station 4 also includes an antenna 15, which upon connection of the mobile portion 3 to the base station 4, is connected to the mobile radio device 7 and thus improves the transmission quality.

The charging device 11 serves to charge up the Li-ion batteries of the mobile portion 3 and at the same time serves as the power supply for the components of the base station 4. The charging device 11 is equipped with a regulator which is suitable for Li-ion batteries, and a monitoring circuit. It is designed for a maximum charging current of 350 mA. It is dimensionally designed, and can be switched to receive a primary ac voltage of 220/110 V, 50/60 Hz, in which respect a range of 100 to 240V for the primary ac voltage and a frequency range of 47–63 Hz is preferred. Protection class 2 is used for the external apparatus 2. The power supply in the base station 4 can also be replaced by a suitable mains plug unit.

The interface device 14 is an infrared interface (IrDA) and the additional antenna 15 is a form of a diversity antenna. The arrangement is provided in each case with suitable $\lambda/4$-antennae which are in the form of a loop or helix antennae.

There is no mains switch. If the base station 4 is to be disconnected from the mains network, the mains plug unit can be pulled out.

The mobile portion 3 is inserted into the base station 4 for the purposes of charging and for data transmission by way of the fixed-line telecommunication network 13.

The base station 4 is equipped with a light-emitting diode which lights up when the mobile portion 3 is plugged in and a charging current is charging the batteries. The light-emitting diode goes out when the mobile portion 3 is removed or the mobile portion 3 is no longer being charged. The display of the light-emitting diode is inverted for the duration of the transmission, but at least one second, when a message is sent or received by way of the installed modem 12. The base station 4 acknowledges insertion of the mobile portion 3 or removal of the mobile portion 3, by a brief sound from a buzzer.

The mobile portion 3 is fully operational during charging in the base station 4. The voltage transformers in the base station 4 are designed to accept up to 40V so that a connection for charging from a motor vehicle system is possible. The control device 5 monitors both the battery voltage and the supply of voltage at the mobile radio module 7.1. When the mobile portion 3 is switched on, the batteries may be charged after about 4 hours in the base station 4.

For the purposes of data transmission, the control device 5 is designed such that after a predetermined number of unsuccessful transmission attempts through the mobile radio device 7, the transmission of data to the monitoring device is effected by way of the fixed-line telecommunication network 13 by means of the interface devices 8 and 14 and the modem 12. Therefore, if the mobile radio device 7 is not operating or the external apparatus 2 is being operated in a country which does not support a mobile radio standard, i.e., there is data in the mobile portion 3 which could be put into intermediate storage in the memory of the SIM-card 7.2, and which could not be transmitted by way of the mobile radio network to the service center, then transmission is effected through the modem 12 as soon as the mobile portion 3 is plugged into the base station 4.

The IR-interface 8 of the mobile portion 3, and the IR-interface 14 of the base station 4 are continuously ready to receive. The mobile portion 3 exchanges data with the base station 4 as soon as it is docked thereto. That means that it is known to the mobile portion 3 in each case whether there is an operational modem 12 in the base station 4.

As the messages to be transmitted involve very short data blocks, a transmission speed of 9600 bauds is sufficient. The modem 12 is either integrated in the base station 4, or if necessary, it can be connected by the service engineer by, a simple snapping engagement into the base station 4. The modem 12 can be switched over to a software handshake as it is only that kind of "optical 2-wire transmission" that is supported by way of the IrDA interfaces 8 and 14.

If an error is detected in operation, a corresponding inquiry from the service center is received, or if the external apparatus 2 goes on the network again after a power-on reset, the external apparatus 2 executes a self-test and signals the result to the service center. Therefore, the external apparatus 2 automatically signals errors and faults, can be checked from the service center, and then the external apparatus 2 signals the service center again when it is again ready for operation (for example after re-charging discharged batteries). The SMS-string with the result of the self-test is only transmitted if the foregoing three preconditions require this, no information relating to the self-test is contained in the normal transmission string.

The purpose of the self-test is to permit conclusions to be drawn about the operation of the hardware. A decision can then be taken in the service center about how any faults and errors should be handled. The external apparatus 2 signals in six cases immediately by way of SMS-messages or alternatively by way of a modem: 1) a dangerous state is being signaled by the pacemaker; 2) the transmission section to the pacemaker is not operable; 3) a self-test of the external apparatus signals a fault or error; 4) upon signaling a low battery state prior to power-off; 5) in the case of a patient alarm, i.e., the patient triggers an alarm by pressing a key of the interface 9; and 6) on a demand by the service center.

The following criteria can be adopted as options in the self-diagnosis of the external apparatus: 1) a check sum by way of the program code (flash-ROM, EEPROM, ROM-error, program incorrectly loaded) gave a memory error; 2) a memory test of the RAM gave a memory error; 3) a temporary failure of the mobile radio network has occurred (can also indicate hardware faults; reading out the mobile radio device 7 can clarify matters here); 4) a time-out in communication with the service center has occurred (as c)); and 5) a received data string is too short or a check sum error has occurred (hardware fault in the telemetry or reception disturbance or range problems).

Only relative time is available for the microprocessors in external apparatuses, with the real-time clock thereof. The time in the implant 1 is not adjusted and after half a year is accurate to +/−0.5 hours so that it cannot be used to establish the system time of the external apparatus 2. If in the mobile portion 3 the battery is discharged or removed by the service engineer, the real-time clock can lose the time data. The external apparatus however requires the current time for specifying that time in connection with data sent to the service center in order to document when events were received from the implant 1.

The data is sent in the form of SMS-messages, and received messages are acknowledged by the service center by way of SMS-messages, to the external apparatus 2. In order to set the current time in the external apparatus 2, i.e., to implement time synchronization of the external apparatus 2, the time signature (SMS-header) of the acknowledgment SMS which contains data and clock time is used. If that acknowledgment SMS comes back within a short time, for example one minute, the external apparatus 2 can set the absolute time in accordance with the header of the acknowledgment, as it is guaranteed that both SMS were on the way for less than a minute. If a longer time has elapsed between the sent SMS and the acknowledgment, the SMS-header of the acknowledgment cannot be evaluated as it is not possible to establish whether the original transmission or the acknowledgment was delayed in transmission. Experience has shown that the time for an SMS-transmission is in the range of about 10 seconds or below so the foregoing procedure can be well applied.

Because there is a very high probability that, after a power-on reset, the clock time in the external apparatus 2 is wrong, immediate time synchronization is provided for that situation. When the external apparatus 2 connects to the network again after a power-on reset, it signals that to the service center straightaway through, an SMS. The clock of the external apparatus can then be immediately set with the SMS-acknowledgment from the service center.

Using this system it is possible ensure that both the service center and also the external apparatus 2 are operated with UTC-time. This means that the entire system operates on one time. Local time such as for example CET or CEST then has to be ascertained from UTC-time when producing doctors' letters.

If problems should arise when ascertaining the absolute time, time transmission by way of the modem 12 can still be used as an alternative. Such a service is generally made available by various providers for the public telephone network.

A service engineer can communicate with the mobile portion 3 using for example a laptop through the interface device 16. In another embodiment, the external apparatus may operate as a data logger insofar as data (for example as a blood sugar monitor) are read in, which are then also sent to the service center by way of SMS.

The range of the interface device 16 is at least 0.4 m. It is arranged in such a way that it can be used by an apparatus which is beside the external apparatus 2, when the mobile portion 3 is docked into the base station 4. It operates bidirectionally and can transmit data in the half duplex mode. The transmission speed of the third interface device 16 is at least 9600 bauds and can then be stepped up to 115 Kbauds.

The third interface device 16 is to be arranged in such a way that the communication between the base station 4 and the mobile portion 3 operates reliably, i.e., there is no possibility that the third interface device 16 can influence the second interface device 8.

Figure 2:
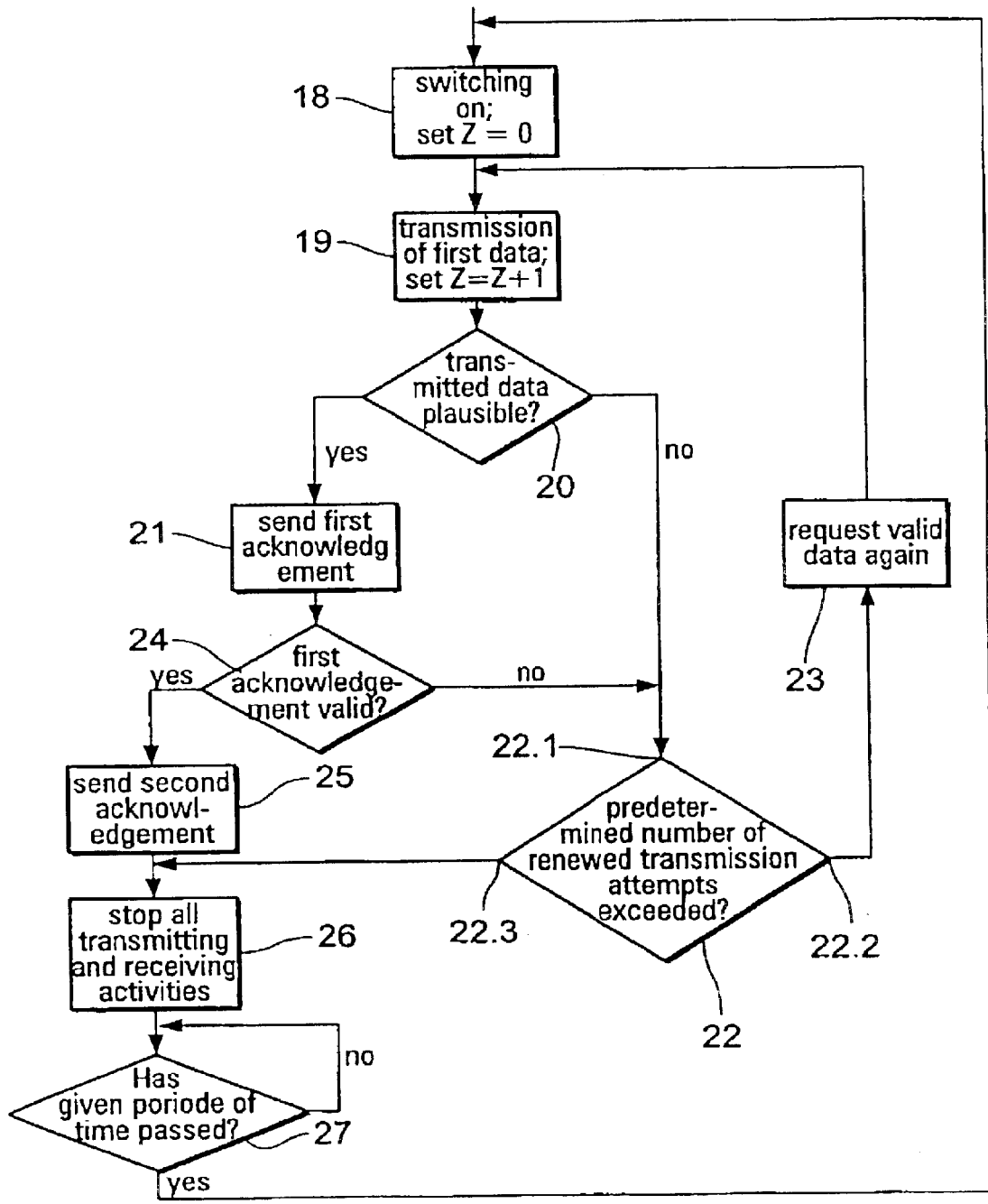
FIG. 2 shows a flow chart of a method according to the invention.

FIG. 2 shows a flow chart of a data transmission method which can be used in conjunction with the method according to the invention and which can be used for data transmission between the implant 1 and the external apparatus 2.

In this embodiment the triggering signal for data transmission is always emitted by the transmitter/receiver unit of the implant 1, for which purpose the transmitter/receiver unit is switched on in a step 18.

In step 19 transmission of the first data is then effected from the implant 1 to the external apparatus 2. A string which comprises 17 bytes is transmitted. This string includes 1 byte for synchronization, 4 bytes for identification, 1 byte for serial the number of the transmission, 1 byte for the length of the string being transmitted, 8 bytes for the data, and 2 bytes for security (CRC). In the case of asynchronous transmission there is an overhead of three bits per byte so that 17"11 bits=187 bits have to be transmitted.

Step 20 involves plausibility checking of the first data transmitted, by the external apparatus. For example, a check of the CRC-bits, in relation to the transmitted string, is conducted, or a check to ascertain whether the synchronization bits have the previously known values. It is also possible to check whether the string length coincides with the sent string length and/or whether the serial number of the transmission is correct. There is no checking of flags, as no handling of the flags takes place in the external apparatus 2. As a result, in the event that the telemetry is expanded, the same type of an external apparatus can always be used. In addition, there is no checking of the implant number as the external apparatus can pass on the information of a plurality of implants.

If the external apparatus in step 20 detects that the data is not plausible, step 22 involves establishing whether a predetermined number of renewed transmission attempts was exceeded.

If it is established in step 22 that the predetermined number of renewed transmission attempts was not exceeded then in step 23 valid data are again requested from the pacemaker. That request can comprise synchronization (8 bits), identification (32 bits), the serial number of the message (8 bits) and an agreed code (8 bits). That string can also be safeguarded with a CRC-byte. 64 bits+83 bits=88 bits are then sent in order to initiate a transmission inquiry of the pacemaker.

If in step 20 the external apparatus detects that the data is plausible, then in step 21, after the plausibility check has been implemented, a first acknowledgment is sent to the implant 1, the first acknowledgment containing a first item of control information for controlling the reception readiness of the first transmitter/receiver unit. If the data set was recognized as being valid, with or in the first acknowledgment a check data set is sent, which is checked in turn by the implant 1. There are two possible options in this circumstance:

First, the previously sent first data set may be sent back completely to the implant 1 which then compares the sent data set to the received data set. Then 187 bits would be sent back again.

Alternatively, synchronization (8 bits), identification (32 bits), the serial number of the transmission (8 bits) and the CRC-bits (16 bits) are sent back for checking purposes to the implant 1 which then checks whether the sent string (identification, number of the transmission) and whether the received CRC-bits conform with the CRC-bits of the sent message. In that case 8 byes are then transmitted instead of 17 bytes as above, that is to say 64 bits+83 bits=88 bits (about half of the information sent in variant 1).

If in step 24 checking of the first acknowledgment in the implant gives a negative result, i.e., if the check data are not identical to the output data, then the first data set is sent again. The implant then tries it again after a fixed period of time. The external apparatus 2 then informs the service center about the number of incorrectly transmitted data packets.

If in step 24 checking of the first acknowledgment in the implant gives a positive result, the implant in step 25 sends a second acknowledgment to the external apparatus 2. That second acknowledgment can comprise synchronization (8 bits), identification (32 bits), the serial number of the message (8 bits) and an agreed code (8 bits). That string can also be safeguarded with a CRC-byte. In this case, 64 bits+8*3 bits=88 bits are sent.

In step 26 the implant 1 stops all transmitting and receiving activities.

In step 27 the passing of a given period of time is checked, after which a fresh data set will be waiting in the implant to be sent.

After receipt of the second acknowledgment the mobile portion 3 will send the first data, which have now been verified, to the service center. The first data set is marked as valid and the service center knows that these data are, with a very high level of probability, correct. The external apparatus retains the first data set until the implant supplies a fresh data set, which is itself verified as being correct.

If an error occurs upon reception of the second acknowledgment (for example different implant number or acknowledgment code is not right) the first data are nonetheless sent by SMS to the service center, but in addition the external apparatus 2 signals that the second acknowledgment of the implant 1 could not be validly transmitted. In this case there is the possibility that the implant 1, after a precisely fixed period of time after dispatch of the second acknowledgment, will go into the receive mode again. Upon a renewed inquiry, the external apparatus 2 can again send the first acknowledgment consisting of 88 bits in order to request a new transmission. Immediately after it has checked that it is addressed, the implant 1 can begin the renewed transmission without the received data first having to be evaluated. In this case, the second acknowledgment or the first data set can be sent again. The external apparatus 2 then has a duplicate copy of either the first data set or the second acknowledgment and it can now decide whether the first data set can be assumed to be valid.

The transmission/reception cycles can be repeated a plurality of times. To save energy, however, it is necessary to ensure that the procedure is interrupted after a given number of transmissions so that the energy storage means of the implant is not unnecessarily discharged. The external apparatus should nonetheless send the data to the service center, but the data must be marked as non-verified. The data are held in the external apparatus 2 until a fresh data set is sent by the implant. In addition, the last valid data set should be kept in the external apparatus, which the service center can then interrogate. In a system in which a plurality of implants co-operate with the external apparatus 2, the respective last data sets of each implant are to be kept in the external apparatus 2.

In one variant of the method, the receiver of the external apparatus 2 is ready at any time to receive data from the implant.

The following point is to be noted with regard to other variants of the method: at regularly recurring or specific moments in time, transmissions are sent from the implant 1 to the external apparatus 2, which either contain data or which only indicate that the implant 1 is active and ready to receive. If more than one message is to be sent, they are sent in succession. These transmissions are received by the external counterpart arrangement, analyzed and acknowledged. The acknowledgments are expected in a fixed time window after transmission so that the receiver in the implant 1 only has to be active for a short time. In fact, in one embodiment data can be transmitted to the implant 1 in the acknowledgments. On the basis of the content and type of the acknowledgments, this indicates whether further data are waiting in the external apparatus 2 for transmission to the implant 1. The acknowledgments are respectively analyzed by the implant 1 to ascertain whether the external apparatus 2 wishes to send further data and it will then automatically proceed with the protocol for the transmission of data in the opposite direction (as described above). This cycle can be repeated as often as may be desired until all data have been transmitted in both directions and no apparatus desires to send further data.

In a further embodiment to an external apparatus having reduced energy consumption, as soon as a message has been received from the external apparatus 2, the implant 1 and the external apparatus are synchronized by establishing time segments whereby periodic times are defined, in which the receiver of the external apparatus is active. The implant 1 may then only transmit within those time segments, if it is to be received. The above-indicated handling instructions are correspondingly modified so that the implant 1 can only send within the time segments and it can no longer send at just any times.

In this embodiment, the time schedule limitation does not apply for an existing communication (sequence of transmissions and acknowledgments) so that the receiver in the external apparatus 2 still remains active for some time after stopping an acknowledgment in order to be able to receive any consequential transmission that may follow from the implant 1. The implant also must not stop a transmission in any time segment. If the external apparatus 2 is to keep contact with a plurality of implants, then specific time segments are managed for each implant involved, and those time segments as far as possible should not overlap in order to avoid interference due to simultaneous transmission from different implants.

The set time segments can be altered within the limits of the above-described normal bidirectional communication both in terms of the duration of the active and also the passive phase, as well as the time of synchronization. If no further transmissions are received from the implant over a given period of time, then the active time segment is increased in length stepwise at the expense of the passive time segment in order to catch any drift divergence of synchronicity. In the extreme case, the receiver in the external apparatus is continuously active. This continuously active state is also the reset state when switching on.

Figure 3:
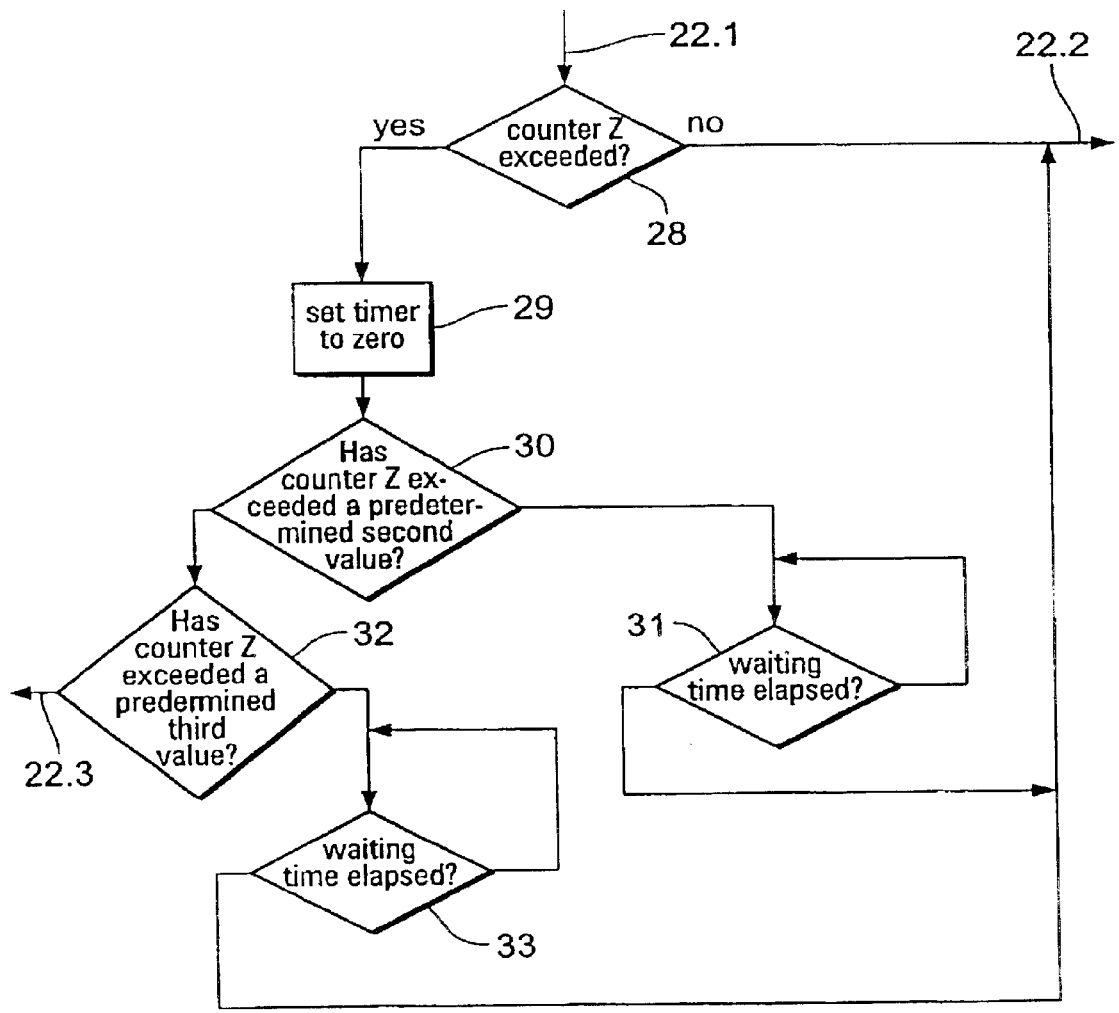
FIG. 3 shows a detail from the flow chart of FIG. 2.

FIG. 3, in the form of a flow chart, shows which strategy can be adopted in the event of repetitions of transmissions by the implant 1. FIG. 3 shows in detail step 22 from FIG. 2 with the input 22.1 and the outputs 22.2 and 22.3.

Step 28 firstly involves checking whether a counter Z has not yet exceeded a predetermined first value, in this case 2. In this respect the counter Z represents the number of transmission attempts executed. In step 18 it is set to zero and it is increased by 1 whenever step 19 is implemented. If the predetermined first value has not yet been exceeded, a new transmission is initiated immediately by way of the output 22.2. Therefore, an attempt is made a second time to send the transmission. If the predetermined first value has been exceeded, then in step 29 a timer is set to zero.

Step 30 then involves checking whether the counter Z has not yet exceeded a predetermined second value, in this case 3. If the predetermined second value has not yet been exceeded the system waits in the waiting loop 31 as a systematic error can be assumed to apply to the transmission. For example, there might be a circumstance which makes the transmission impossible for some time (for example a piece of electrical equipment which is not adequately interference-suppressed). After a waiting time of for example 5 minutes, a further transmission attempt is started. If this is also unsuccessful the cycle is continued at step 78.

Step 32 then involves checking whether the counter Z has not yet exceeded a predetermined-third value, in this case 4. If the predetermined third value is not yet exceeded the system waits even longer through the waiting loop 33, for example 1 hour, and starts a last transmission attempt. If this is also unsuccessful, the cycle is continued at step 28 and thereafter left at 22.3. In this case a transmission is only attempted again when fresh data are ready for transmission in the pacemaker.

Figure 4:
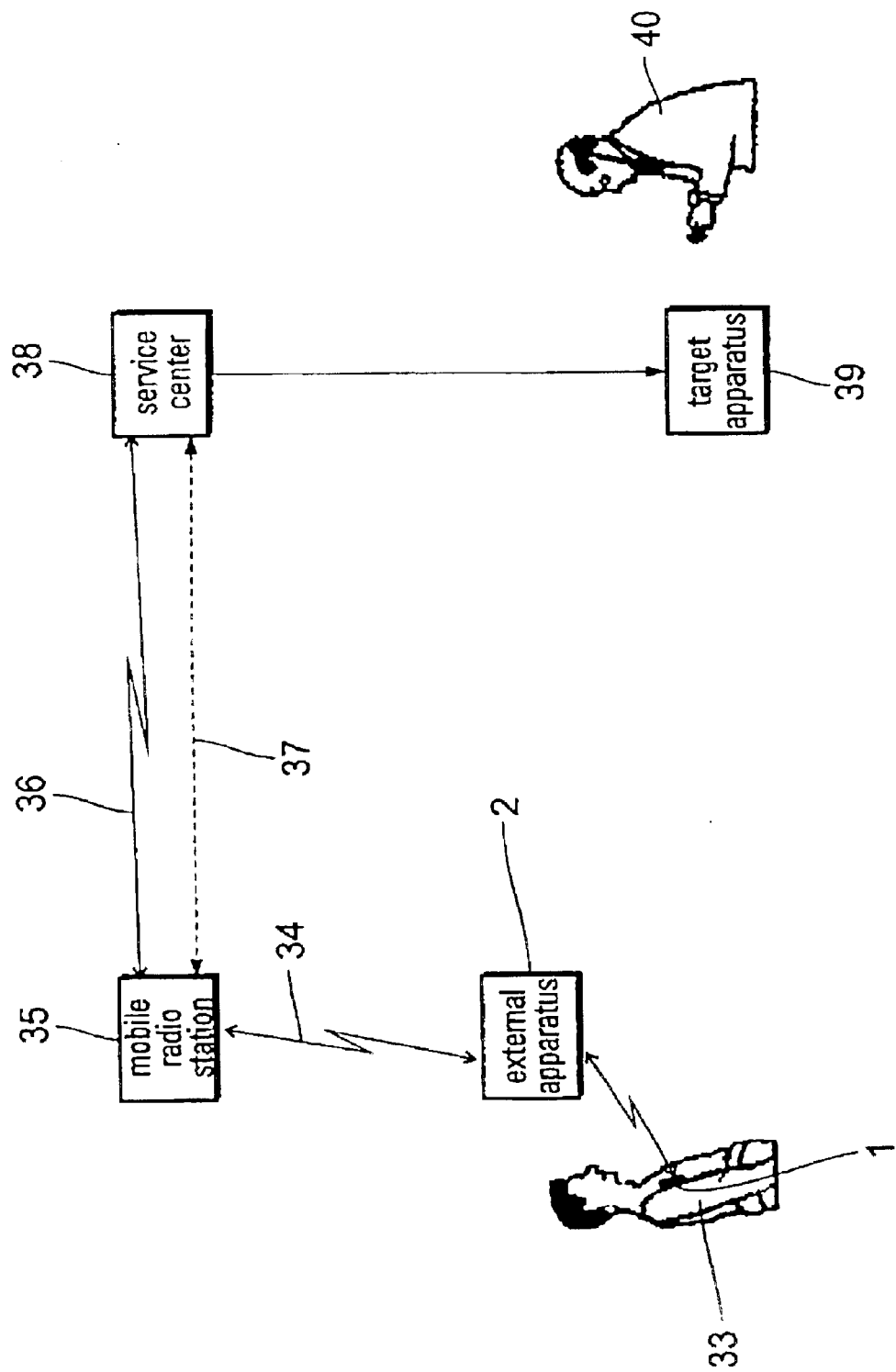
FIG. 4 shows a block circuit diagram of an embodiment of a patient monitoring system according to the present invention.

FIG. 4 shows a block circuit diagram of one embodiment of a patient monitoring system using the present invention. In this case data transmission takes place between the implant 1 and the external apparatus shown in FIG. 1, the implant 1 being worn by a patient 33. From the external apparatus 2, the read-out data are transmitted by way of a mobile radio section 34 of a mobile radio network to a mobile radio station 35 of the mobile radio network and from there sent also by way of a mobile radio section 36 or alternatively by way of a fixed-line network connection 37 to a service center 38 which serves as a central storage and monitoring center. In this case all data are sent in the form of SMS-messages and mutually acknowledged by way of SMS.

In this embodiment, the central storage unit 38 is provided with a fully automatic database. The medical data are automatically read by way of TCP/IP-connection into the database computer where they are respectively entered into the provided tables and table fields including: moment in time, implant, patient, external apparatus and medical contact (doctor/clinic)

When a specified portion of the database is filled, the data are transferred from the computer onto external media (for example CD or tape). In accordance with the medical guidelines for data security, patient-related data are stored immediately (as far as may be possible) on-external read only media (e.g., CD-ROM). Proper access to all externally safeguarded data is then made possible by way of suitable references in the database.

The access options to the data are regulated by complex rights allocation (for example, reading, writing, modifying, erasing, etc.) for various user groups such as data managers, clinic or doctor. During operation of the database manual interventions and inquiries by system operators and other clients (for example, the doctor 40) are possible at any time.

Priority-controlled triggers in the database and a coupled expert system make it possible to react specifically to medical facts and situations. During operation of such a system, the database generates, in accordance with pre-defined rules, items of information for the doctor and the system operator and passes such information co the target apparatuses 39 by way of fax, e-mail, and internal or external computer connections. The items of information which are outputted are kept for later collective inquiry in the database, in that way the doctor can again request a summarizing or lost report of a particular patient. And in use the doctor receives medical information in a few minutes, even during an examination, and the doctor also receives summarized information relating to the next after-care date. The transmission medium and the target addresses can in this case be configured independently of the triggering time and event. In that way, the attending doctor 40 can obtain information about the state his patient's 33 health in a desired manner.

In an emergency, the patient 33 can also receive medical help more quickly than usual. That emergency situation is triggered both by objectively measured medical data and also by depressing a key on the mobile portion 3. In such a system, the patient request enjoys highest priority, in relation to the other events.

In addition, the database can also react separately to data transmissions which are triggered by the patient, for example, where information is sent to the doctor and the system operator. In that way, the subjective condition of the patient can be taken into account in the data acquisition procedure, and incorporated into the diagnosis options.

Figure 5:
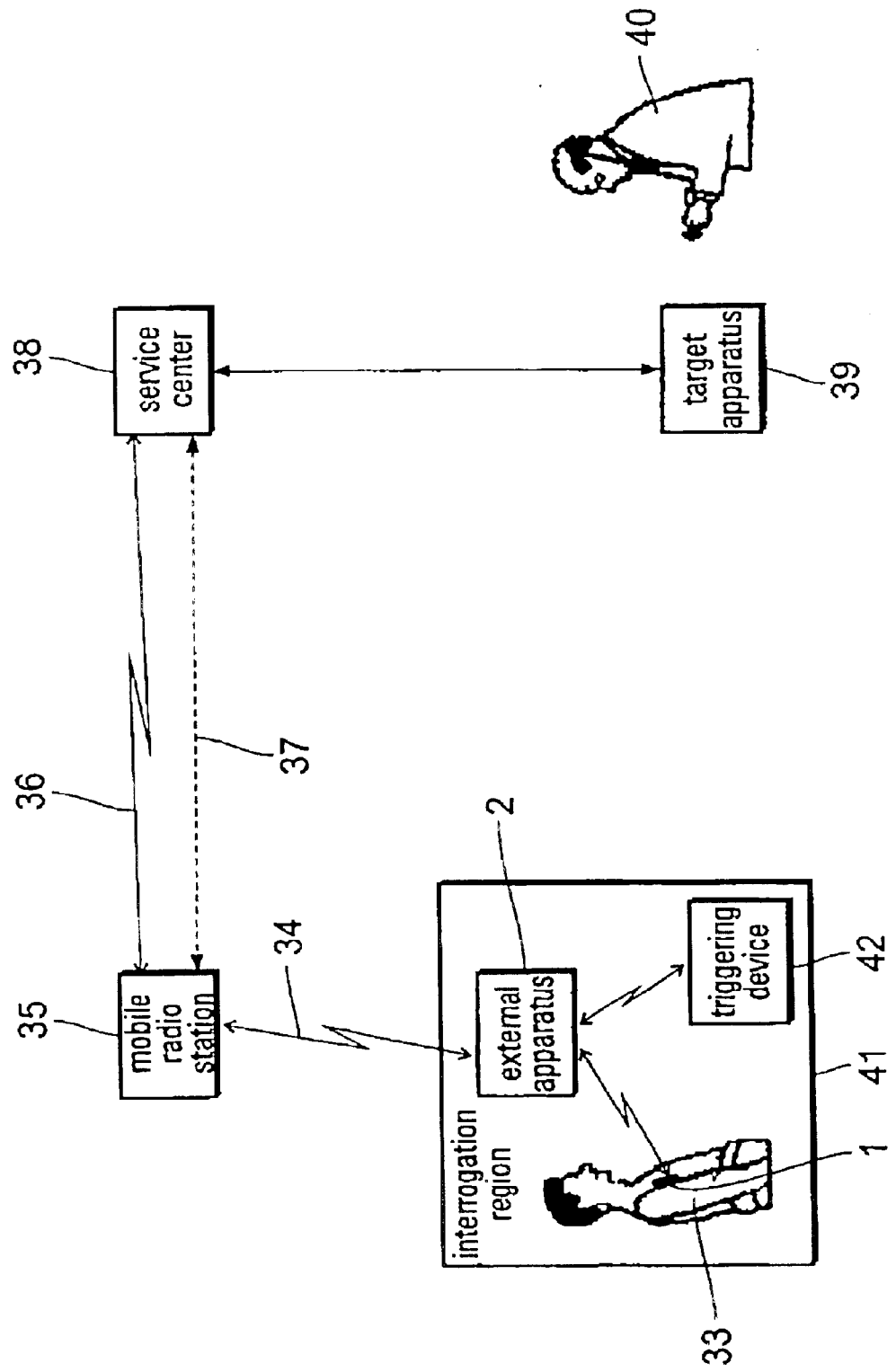
FIG. 5 shows a block circuit diagram of an embodiment of a patient monitoring and after-care system according to the present invention.

FIG. 5 shows a block circuit diagram of a variant of a patient monitoring and after-care system using the present invention. In this case, the patient 33 with the implant 1 and the external apparatus 2 for after-care investigation are disposed in the interrogation region 41 of an after-care arrangement. In this case the process is triggered by the triggering device 42 which co-operates with the external apparatus 2 upon entering the interrogation region 41. In such a system, interrogation of the first data from the implant 1 is automatically executed by the doctor 40 prior to the after-care examination and transmission of the first data is effected by means of the long-range telemetry connection between the implant 1 and the external apparatus 2.

The result of the interrogation passes in a suitably processed form by way of the path described in relation to FIG. 4 by way of the service center 38 to the target apparatus 39 from which it is outputted to the doctor 40 for his review. At the same time, further patient-related data are also outputted from the database of the service center 38 so that the doctor 40 can form a comprehensive picture.

The routine current investigation by the doctor is thus supplemented by an overall picture over the time since the last visit to the doctor. The doctor acquires a picture over a number of weeks or months, which is substantially more informative than the information obtained during the current examination. In such an embodiment, a good picture is formed of the lifestyle habits of the patient, whereas it is precisely the appointment with the doctor that can represent an exceptional situation from the usual lifestyle (travel to the clinic or to the doctor, going up stairs, stress in traffic etc.).

During the actual examination the doctor (for example in carrying out stress tests) can also immediately request a report from the service center 38, which is then supplied after a few minutes. In that way parameter changes which were set by means of the programmer can be immediately checked and potentially optimized. Further reports can be produced by virtue of storage in the database and further evaluation options by the expert system or by comparison with other cases. In that way, due to advances in medical knowledge, it is possible to recognize new correlations. These evaluations are then sent to the doctor in the next report, without the doctor having to check each of his patients for possible effects and consequences when fresh knowledge comes to light.

In another embodiment of the invention, it is additionally possible, to automatically give standard tests or diagnosis programs which are normally only carried out under medical supervision as soon as the patient 33 enters the interrogation region 41 of an after-care arrangement. It is possible, for example, to implement stimulus threshold, sensitivity, stress or defibrillation-shock tests.

Figure 6:
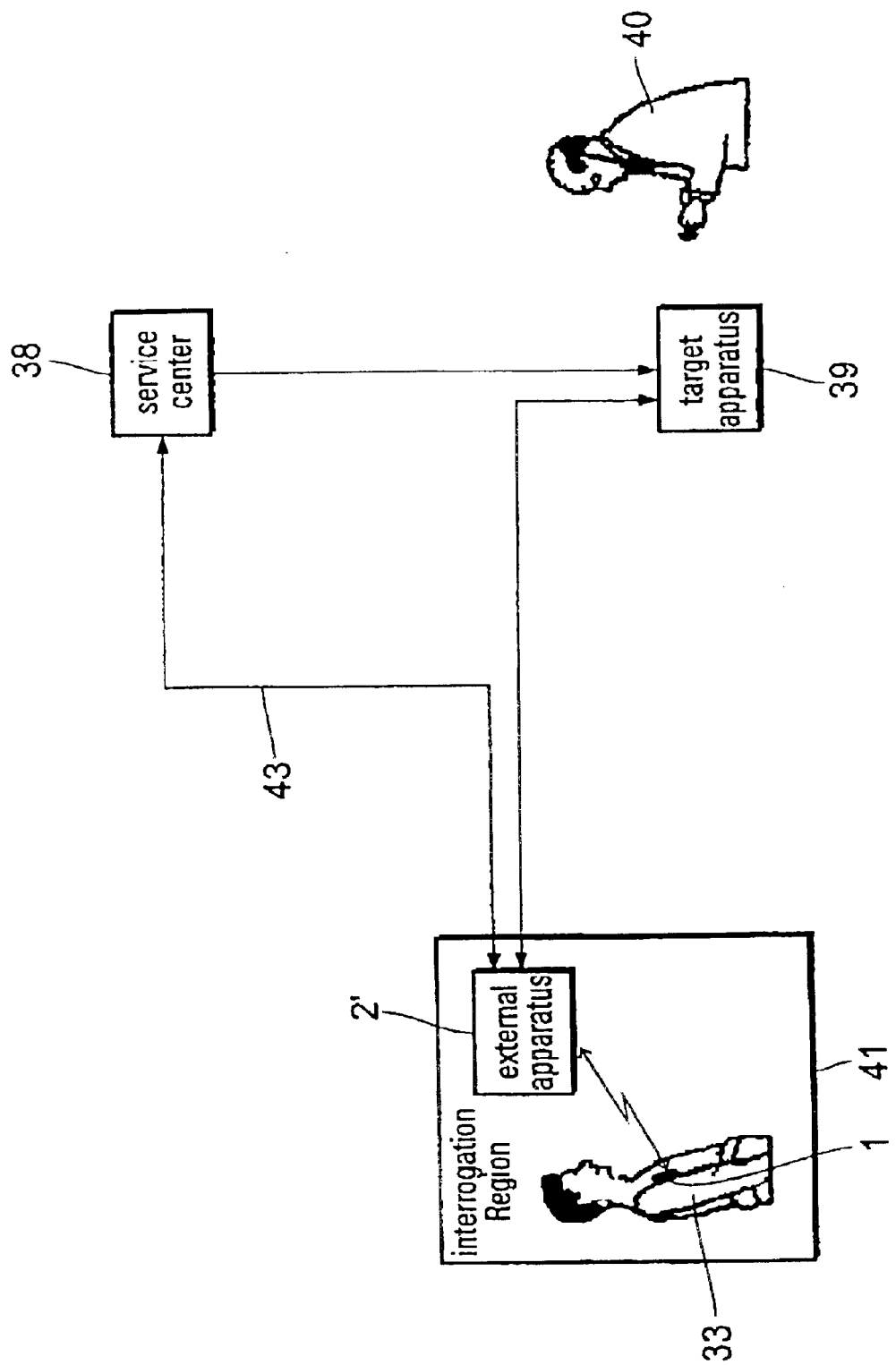
FIG. 6 shows a block circuit diagram of an embodiment of a patient monitoring and after-care system according to the present invention.

FIG. 6 shows a variant of the invention from FIG. 5 in which an external apparatus 2' is fixedly installed in the interrogation region 41 of the after-care arrangement. In this case the interrogation procedure is triggered as soon as the patient 33 with the implant 1 is in the interrogation range of the external apparatus 2' for a certain period of time.

The result of the interrogation procedure goes in a suitably processed form directly from the external apparatus 2' to the target apparatus 39 from which it is outputted to the doctor 40 for his review. At the same time, further patient-related data are also acquired by way of the connection 43 from the database of the service center 38 and outputted at the target apparatus 39 so that the doctor 40 can have a comprehensive picture of the patient's health.

Figure 7:
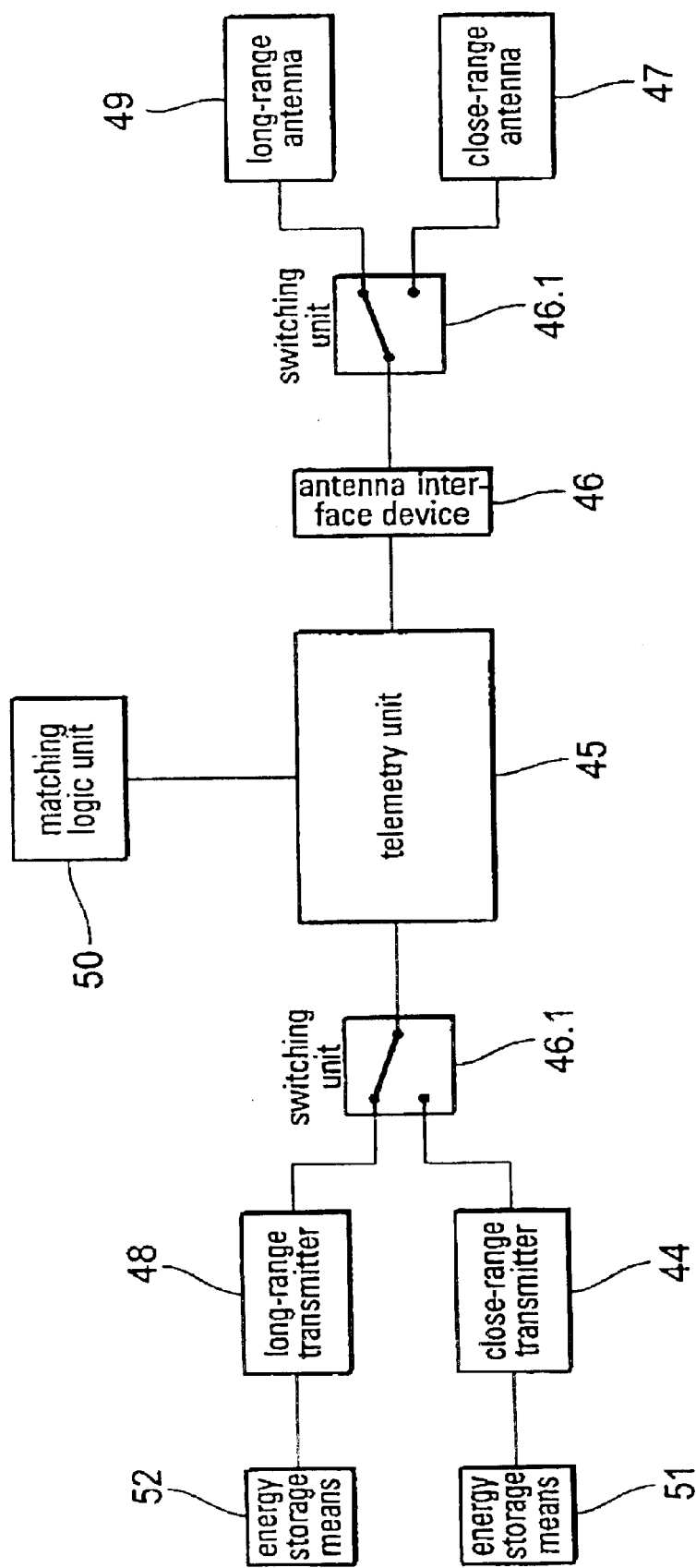
FIG. 7 shows a block circuit diagram of an embodiment of a telemetry device of an electromedical implant according to the present invention.

FIG. 7 shows a block circuit diagram of a telemetry device of an electromedical implant which can be used together with the present invention. The telemetry device has a close range transmitter 44, a telemetry unit 45 connected thereto and an antenna interface device 46 which is connected to the telemetry unit 45 and by way of which a close-range antenna 47 is connected to the close-range transmitter/receiver unit 44.

In addition, to allow for long-range telemetry, the arrangement also has a long-range transmitter 48 connected to the telemetry unit 45 and a long-range antenna 48 connected to the antenna interface device 46.

Furthermore, the close-range telemetry device and the long-range telemetry device have separate energy storage means 51 and 52.

The other necessary system components for a telemetry device such as intermediate storage means, operational control, encoding, decoding and driver with threshold detector are in this case integrated in the telemetry unit 45.

For switching between the long-range transmitter 48 and the close-range transmitter 44, the units are connected to the telemetry unit 45 by way of a switching unit 46.1. For switching over between the close-range antenna 47 and the long-range antenna 49, the antennae are connected to the antenna interface device 46 by way of a further switching unit 46.2. However, it will be appreciated that in other variants, the two transmitters, like the two antennae, can be connected in parallel to the telemetry unit 45 and the antenna interface unit 46 as in general the close-range and long-range telemetry are not operated simultaneously.

To provide for adaptation of the modulation method for the respective telemetry involved, the arrangement has a matching logic unit 50 which is connected to the telemetry unit 45. The long-range telemetry device is operated at substantially, the same effective data rate as the close-range telemetry device.

Figure 8:
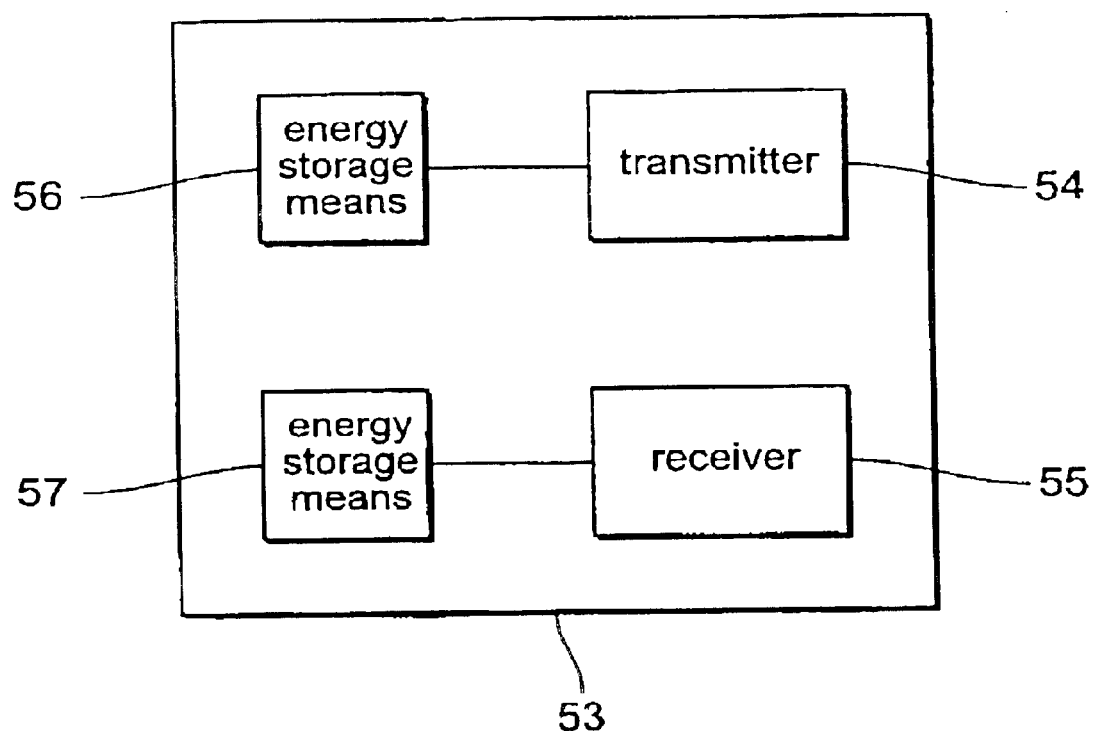
FIG. 8 shows the transmitter/receiver unit of the embodiment shown in FIG. 1.

FIG. 8 shows the transmitter/receiver unit of an embodiment of the implant 1, in which separate energy storage means 56 and 57 are provided for the transmitter 54 and the receiver 55. The energy storage means involve separate buffer capacitors 56 and 57. These capacitors 56 and 57 only have to be charged to the level necessary for the respective procedure. Accordingly, the energy consumption of the one procedure does not influence the energy supply for the other procedure. The procedures can thus directly follow each other, which is advantageous in relation to a bidirectional communication protocol without charging of a single buffer capacitor to double the energy content being necessary for that purpose.

Figure 9:
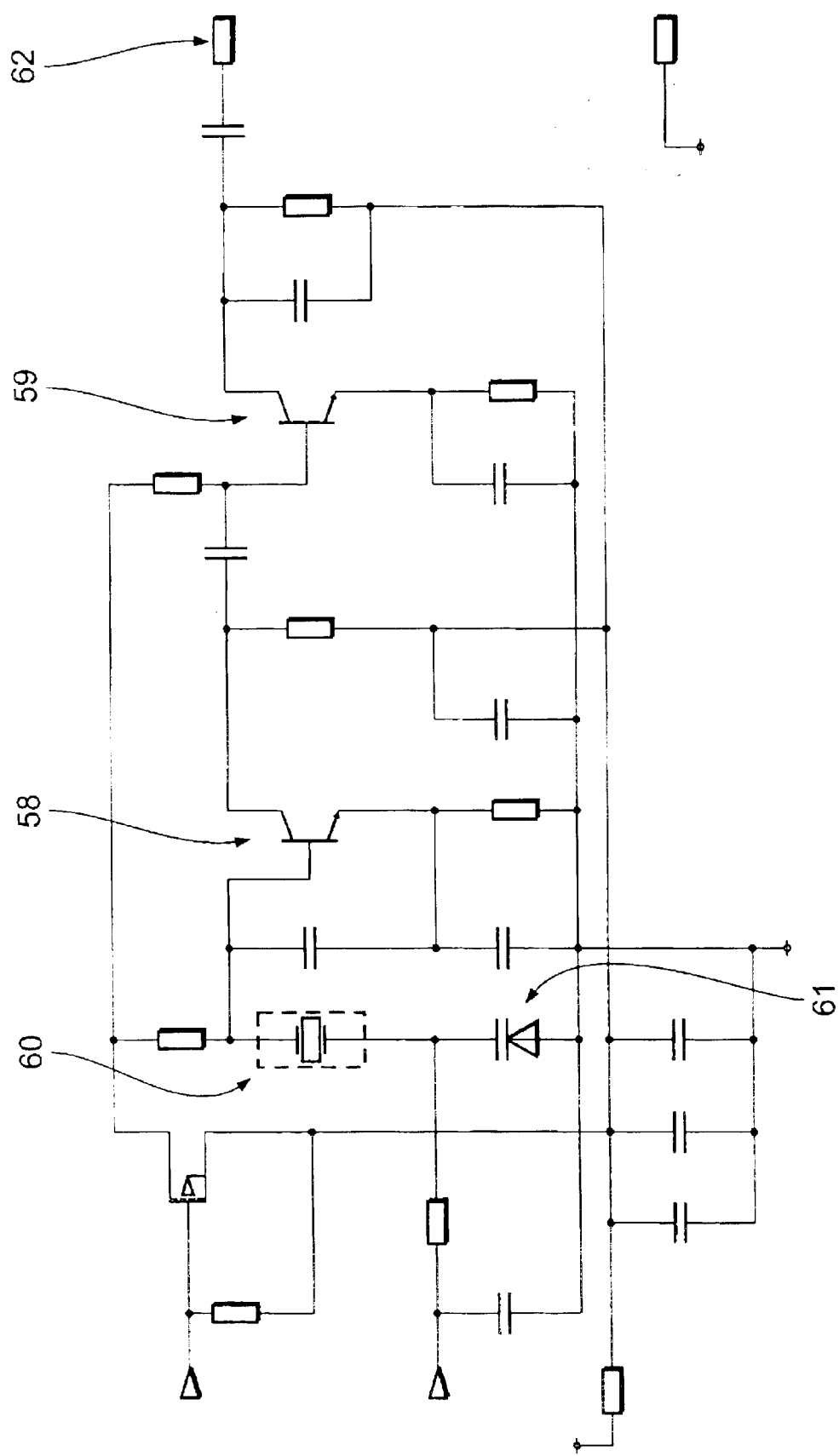
FIG. 9 shows a circuit diagram of an embodiment of a transmitter used in the embodiment of FIG. 1.

FIG. 9 shows a circuit diagram of a transmitter according to the invention of the first transmitter/receiver unit of a variant of the implant from FIG. 1. In this case a stable, frequency-modulatable transmitter has been embodied by means of two bipolar transistors 58, 59, wherein the first transistor 58 in a Col-pitts or Clapp circuit with an SAW-resonator 60 forms an SAW-stabilized oscillator, and the second transistor 59 serves as a buffer stage and antenna driver. The transistors 58, 59 are designed for maximum gain at lowest collector current. The frequency can be modulated by a capacitance diode 61 in series with the SAW-resonator 60. The frequency variation and thus the data rate and/or the range of the transmitter can be increased. In such a case the capacitance diode is replaced by a PIN-diode which is switched by a further transistor.

The antenna used can be a simple wire loop or an open wire (throw-out antenna) in the contour of the header of the implant. Overall in this case, at 400 MHz a current consumption of less than 1 mA is possible, at a range of several meters. The circuit can be supplied directly from a buffer capacitor fed by a high-resistance battery of the implant 1, or from a low-resistance battery. There is no need for a charge pump.

Figure 10:
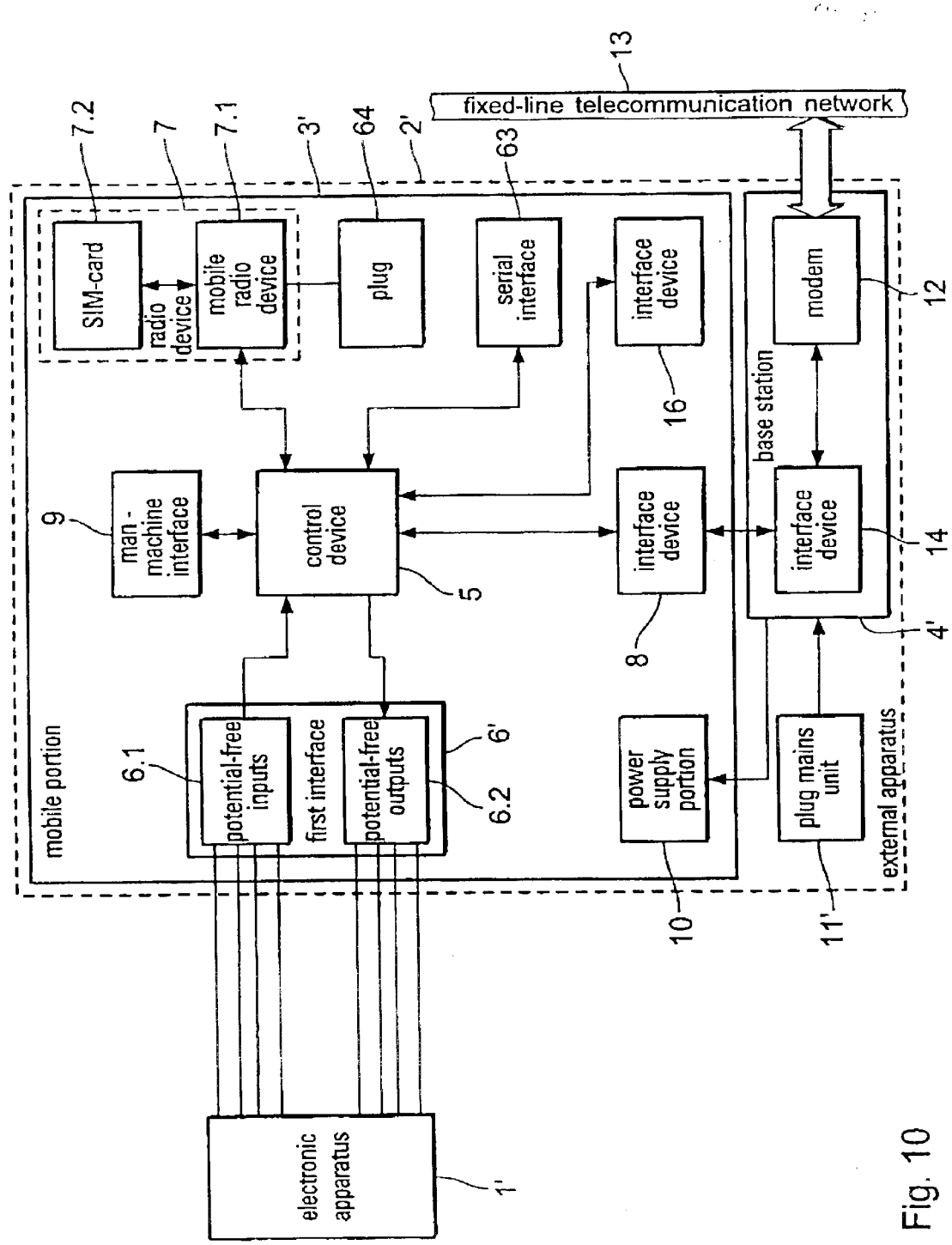
FIG. 10 shows a block circuit diagram of an embodiment of an apparatus according to the invention.

FIG. 10 shows a further embodiment of an apparatus according to the invention which substantially corresponds to that shown in FIG. 1, for which reason reference will only be made here to the differences involved. This arrangement involves an external apparatus 2" which is suitable for monitoring, actuating, and transmitting data from various electronic apparatuses 1'. Uses of this systems can include the remote monitoring of installations, for example, the degree of filling of automatic drink dispensers or automatic vending machines; a link with domestic technology, for example the control and monitoring of an air conditioning installation or a heating system; coupling to alarm installations or glass breakage signaling installations, for example burglary signaling by way of mobile radio; coupling to measurement systems, for example weather stations and level metering units on rivers; coupling to systems for traffic observation and control, for example traffic signs, bridges etc. It can also be used as a bugging system or as a mobile telephone with special digital functions.

The differences in relation to the structure shown in FIG. 1 essentially concern the mobile portion 3' of the external apparatus 2". In this case, the first interface device includes four potential-free inputs 6.1 by way of optocouplers and four potential-free outputs 6.2. By virtue of the potential separation of the inputs and outputs 6.1 and 6.2, the external apparatus 2" is suitable for monitoring and controlling digital states.

In addition, the receiving and transmitting portion 6 of FIG. 1 is not included here, instead the serial interface 63 (RS 232), which is thus liberated, is taken out by way of a 9-pole plug. In the case of the RS 232 a software handshake with three lines (RXD, TXD, GND) is sufficient. That means that the transmission rate is also limited to 9600 bauds. The serial interface 63 is not designed to be potential-free. By way of a further plug 64 the connections of the mobile radio module 7.1 can be taken to a microphone, a loudspeaker, and optionally a buzzer (6 lines) so that for further areas of use it is possible to add a listening/speech combination and a buzzer.

The inputs 6.1 are in a first range between −3V and 1.5V L-level, between 3.5 and 8V H-level and 10 mA input current; while in a second range they are at between −3V and 78V L-level, between 18V and 30V H-level and 10 mA input current. State recognition is implemented by way of an LED-display at a maximum switching frequency of 100 Hz rectangular and a separation voltage of 2.5 kV.

The outputs have between 15 and 30V DC separate voltage feed, a load current of 200 mA, short-circuit protection, protection from thermal overloading and a separation voltage of 2.5 kV. Potential separation is effected by way of opto-couplers and the power switching function by way of MOS-FETs.

The difference in the structure shown in FIG. 1, of the base station 4', arises in regard to having the power supplied by the plug mains unit 11, instead of the mains unit in the base station. A further possible configuration provides that the base station is omitted and the external apparatus is supplied directly by way of a mains unit. In the event of mains failure, the mobile portion then still continues to operate for about 20 hours.

The invention is not limited in terms of implementation thereof to the preferred embodiments set forth hereinbefore. On the contrary, a large number of alternative configurations are possible, which make use of the illustrated structure even in configurations of a basically different kind.

What is claimed is:

1. An electromedical implant capable of exchanging data with an external apparatus, the implant comprising a telemetry device for the exchange of data with the external apparatus and at least two power supply buffer capacitors coupled to the telemetry device, wherein the telemetry device comprises a telemetry transmitter and a telemetry receiver, and wherein the telemetry transmitter is provided with one of the at least two power supply buffer capacitors for providing sufficient energy for the telemetry transmitter to transmit data, and the telemetry receiver is provided with a separate one of the at least two power supply buffer capacitors for providing sufficient energy for the telemetry receiver to receive data.

2. The implant as set forth in claim 1 wherein the power supply buffer capacitor provided for the telemetry transmitter holds a charge just sufficient for the telemetry transmitter to transmit data, and wherein the power supply buffer capacitor for the telemetry receiver holds a charge just sufficient for the telemetry receiver to receive data.

3. The implant as set forth in claim 2 wherein the power supply buffer capacitor for the telemetry transmitter and the power supply buffer capacitor for the telemetry receiver are of different sizes.

4. The implant as set forth in claim 2 wherein the telemetry device charges the power supply buffer capacitors either together or individually.

5. The implant as set forth in claim 1 wherein the power supply buffer capacitor for the telemetry receiver is further connected to the telemetry transmitter such that said power supply buffer capacitor for the telemetry receiver further operates as a reserve power supply buffer capacitor for the telemetry transmitter.

6. The implant as set forth in claim 1 wherein the power supply buffer capacitor for the telemetry receiver and the power supply buffer capacitor for the telemetry transmitter are connected either in parallel or in series with each other.

7. The implant as set forth in claim 1 wherein the implant is selected from the group consisting of: a cardiac pacemaker, a defibrillator, and a cardioverter.

8. An electromedical implant capable of exchanging data with an external apparatus, the implant comprising a telemetry device for the exchange of data with the external apparatus and at least two power supply buffer capacitors coupled to the telemetry device, wherein the telemetry device comprises a telemetry transmitter and a telemetry receiver, and wherein the telemetry transmitter is provided with one of the at least two power supply buffer capacitors for providing sufficient energy for the transmission of data, and the telemetry receiver is provided with a separate one of the at least two power supply buffer capacitors for providing sufficient energy for the reception of data, the implantable device is adapted to immediately charge up the power supply buffer capacitor for providing sufficient energy for the transmission of data prior to such transmission, and to immediately charge up the power supply buffer capacitor for providing sufficient energy for the reception of data prior to such reception.

9. An electromedical implant capable of exchanging data with an external apparatus, the implant comprising a telemetry device for the exchange of data with the external apparatus and at least two power supply buffer capacitors coupled to the telemetry device, wherein the telemetry device comprises a telemetry transmitter and a telemetry receiver, and wherein the telemetry transmitter is provided with one of the at least two power supply buffer capacitors for providing sufficient energy for the transmission of data, and the telemetry receiver is provided with a separate one of the at least two power supply buffer capacitors for providing sufficient energy for the reception of data, wherein the power supply buffer capacitor for the telemetry transmitter is further connected to the telemetry receiver such that said power supply buffer capacitor for the telemetry transmitter further operates as a reserve power supply buffer capacitor for the telemetry receiver.

10. An electromedical implant capable of exchanging data with an external apparatus, the implant comprising a telemetry device for the exchange of data with the external apparatus, a battery and at least two power supply buffer capacitors coupled to the telemetry device, wherein the telemetry device comprises a telemetry transmitter and a telemetry receiver, and wherein the telemetry transmitter is provided with one of the at least two power supply buffer capacitors for providing sufficient energy for the telemetry transmitter to transmit data, and the telemetry receiver is provided with a separate one of the at least two power supply buffer capacitors for providing sufficient energy for the telemetry receiver to receive data, wherein the at least two power supply buffer capacitors are further coupled to the battery.

* * * * *